(12) United States Patent
Kennedy, II

(10) Patent No.: US 7,967,818 B2
(45) Date of Patent: Jun. 28, 2011

(54) CAUTERY CATHETER

(75) Inventor: Kenneth C. Kennedy, II, Clemmons, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 962 days.

(21) Appl. No.: 11/450,078

(22) Filed: Jun. 8, 2006

(65) Prior Publication Data

US 2007/0118112 A1 May 24, 2007

Related U.S. Application Data

(60) Provisional application No. 60/689,672, filed on Jun. 10, 2005.

(51) Int. Cl.
*A61B 18/14* (2006.01)

(52) U.S. Cl. .............................. 606/45; 606/49

(58) Field of Classification Search .............. 606/41, 606/45–49
See application file for complete search history.

(56) References Cited

U.S. PATENT DOCUMENTS

| | | | |
|---|---|---|---|
| 2,508,690 A | 5/1950 | Schmerl | |
| 4,133,315 A | 1/1979 | Berman et al. | |
| 4,134,405 A | 1/1979 | Smit | |
| 4,246,893 A | 1/1981 | Berson | |
| 4,315,509 A | 2/1982 | Smit | |
| 4,403,604 A | 9/1983 | Wilkinson et al. | |
| 4,416,267 A | 11/1983 | Garren et al. | |
| 4,485,805 A | 12/1984 | Foster, Jr. | |
| 4,558,699 A | 12/1985 | Bashour | |
| 4,607,618 A | 8/1986 | Angelchik | |
| 4,694,827 A | 9/1987 | Weiner et al. | |
| 4,696,288 A | 9/1987 | Kuzmak et al. | |
| 4,723,547 A | 2/1988 | Kullas et al. | |
| 4,803,985 A | 2/1989 | Hill | |
| 4,878,905 A | 11/1989 | Blass | |
| 4,885,003 A * | 12/1989 | Hillstead | 604/22 |
| 4,899,747 A | 2/1990 | Garren et al. | |
| 4,925,446 A | 5/1990 | Garay et al. | |
| 4,952,339 A | 8/1990 | Temus et al. | |
| 5,129,915 A | 7/1992 | Cantenys | |
| 5,190,058 A * | 3/1993 | Jones et al. | 128/898 |
| 5,226,430 A * | 7/1993 | Spears et al. | 128/898 |
| 5,234,454 A | 8/1993 | Bangs | |
| 5,246,456 A | 9/1993 | Wilkinson | |
| 5,306,300 A | 4/1994 | Berry | |
| 5,327,914 A | 7/1994 | Shlain | |
| 5,345,949 A | 9/1994 | Shlain | |
| 5,653,684 A * | 8/1997 | Laptewicz et al. | 604/22 |
| 5,868,141 A | 2/1999 | Ellias | |

(Continued)

FOREIGN PATENT DOCUMENTS

| | | |
|---|---|---|
| EP | 0137 878 | 11/1983 |
| WO | WO 2004087249 A2 * | 10/2004 |

*Primary Examiner* — Linda C Dvorak
*Assistant Examiner* — Amanda Scott
(74) *Attorney, Agent, or Firm* — Brinks Hofer Gilson & Lione

(57) ABSTRACT

A cautery catheter is described having an expandable and electrically conductive mesh that can cauterize treatment sites having large effective surface areas. The mesh is composed of interwoven filaments which are aligned with the cautery catheter in an unexpanded state. Reorientation of the filaments of the mesh enables expansion of the mesh. When the expanded mesh contacts the desired treatment area, an electrocautery unit supplies electrical energy to the filaments of expanded mesh to cauterize the treatment site.

26 Claims, 5 Drawing Sheets

U.S. PATENT DOCUMENTS

| | | | |
|---|---|---|---|
| 5,938,669 A | 8/1999 | Klaiber et al. | |
| 5,993,473 A | 11/1999 | Chan et al. | |
| 6,067,991 A | 5/2000 | Forsell | |
| 6,210,347 B1 | 4/2001 | Forsell | |
| 6,238,389 B1 * | 5/2001 | Paddock et al. | 606/41 |
| 6,427,089 B1 | 7/2002 | Knowlton | |
| 6,450,946 B1 | 9/2002 | Forsell | |
| 6,454,699 B1 | 9/2002 | Forsell | |
| 6,460,543 B1 | 10/2002 | Forsell | |
| 6,511,490 B2 | 1/2003 | Robert | |
| 6,540,789 B1 | 4/2003 | Silverman et al. | |
| 6,558,400 B2 | 5/2003 | Deem et al. | |
| 6,627,206 B2 | 9/2003 | Lloyd | |
| 6,656,194 B1 | 12/2003 | Gannoe et al. | |
| 6,675,809 B2 | 1/2004 | Stack et al. | |
| 6,676,674 B1 | 1/2004 | Dudai | |
| 6,733,512 B2 | 5/2004 | McGhan | |
| 6,740,121 B2 | 5/2004 | Geitz | |
| 6,746,460 B2 | 6/2004 | Gannoe et al. | |
| 6,748,953 B2 * | 6/2004 | Sherry et al. | 128/898 |
| 6,755,869 B2 | 6/2004 | Geitz | |
| 6,802,868 B2 | 10/2004 | Silverman et al. | |
| 6,845,776 B2 | 1/2005 | Stack et al. | |
| 6,879,859 B1 | 4/2005 | Boveja | |
| 6,916,326 B2 | 7/2005 | Benchetrit | |
| 6,946,002 B2 | 9/2005 | Geitz | |
| 6,981,980 B2 | 1/2006 | Sampson et al. | |
| 6,994,715 B2 | 2/2006 | Gannoe et al. | |
| 7,033,373 B2 | 4/2006 | de la Torre et al. | |
| 7,033,384 B2 | 4/2006 | Gannoe et al. | |
| 7,037,344 B2 | 5/2006 | Kagan et al. | |
| 7,054,690 B2 | 5/2006 | Imran | |
| 7,056,305 B2 | 6/2006 | Garza Alvarez | |
| 7,066,945 B2 | 6/2006 | Hashiba et al. | |
| 7,090,699 B2 | 8/2006 | Geitz | |
| 7,097,665 B2 | 8/2006 | Stack et al. | |
| 7,112,186 B2 | 9/2006 | Shah | |
| 7,121,283 B2 | 10/2006 | Stack et al. | |
| 7,152,607 B2 | 12/2006 | Stack et al. | |
| 7,172,613 B2 | 2/2007 | Wazne | |
| 7,175,638 B2 | 2/2007 | Gannoe et al. | |
| 7,177,693 B2 | 2/2007 | Starkebaum | |
| 7,255,695 B2 * | 8/2007 | Falwell et al. | 606/41 |
| 2001/0001314 A1 * | 5/2001 | Davison et al. | 606/41 |
| 2001/0011543 A1 | 8/2001 | Forsell | |
| 2002/0188354 A1 | 12/2002 | Peghini | |
| 2003/0049325 A1 | 3/2003 | Suwelack et al. | |
| 2003/0109892 A1 | 6/2003 | Deem et al. | |
| 2003/0120265 A1 | 6/2003 | Deem et al. | |
| 2003/0158564 A1 | 8/2003 | Benchetrit | |
| 2003/0199989 A1 | 10/2003 | Stack et al. | |
| 2003/0199990 A1 | 10/2003 | Stack et al. | |
| 2003/0199991 A1 | 10/2003 | Stack et al. | |
| 2003/0229340 A1 * | 12/2003 | Sherry et al. | 606/27 |
| 2004/0019388 A1 | 1/2004 | Starkebaum | |
| 2004/0024386 A1 | 2/2004 | Deem et al. | |
| 2004/0039452 A1 | 2/2004 | Bessler | |
| 2004/0044353 A1 | 3/2004 | Gannoe | |
| 2004/0044354 A1 | 3/2004 | Gannoe et al. | |
| 2004/0049209 A1 | 3/2004 | Benchetrit | |
| 2004/0082963 A1 | 4/2004 | Gannoe et al. | |
| 2004/0092892 A1 | 5/2004 | Kagan et al. | |
| 2004/0092974 A1 | 5/2004 | Gannoe et al. | |
| 2004/0117031 A1 | 6/2004 | Stack et al. | |
| 2004/0122452 A1 | 6/2004 | Deem et al. | |
| 2004/0122453 A1 | 6/2004 | Deem et al. | |
| 2004/0122526 A1 | 6/2004 | Imran | |
| 2004/0138760 A1 | 7/2004 | Schurr | |
| 2004/0138761 A1 | 7/2004 | Stack et al. | |
| 2004/0143342 A1 | 7/2004 | Stack et al. | |
| 2004/0153106 A1 | 8/2004 | Dudai | |
| 2004/0158331 A1 | 8/2004 | Stack et al. | |
| 2004/0181140 A1 * | 9/2004 | Falwell et al. | 600/374 |
| 2004/0186503 A1 | 9/2004 | DeLegge | |
| 2004/0220560 A1 * | 11/2004 | Briscoe | 606/32 |
| 2004/0220682 A1 | 11/2004 | Levine et al. | |
| 2004/0243152 A1 | 12/2004 | Taylor et al. | |
| 2005/0049718 A1 | 3/2005 | Dann et al. | |
| 2005/0096750 A1 | 5/2005 | Kagan et al. | |
| 2005/0149141 A1 | 7/2005 | Starkebaum | |
| 2005/0149142 A1 | 7/2005 | Starkebaum | |
| 2005/0177181 A1 | 8/2005 | Kagan et al. | |
| 2005/0192531 A1 | 9/2005 | Birk | |
| 2005/0192614 A1 | 9/2005 | Binmoeller | |
| 2005/0209653 A1 | 9/2005 | Herbert et al. | |
| 2005/0222637 A1 | 10/2005 | Chen | |
| 2005/0222638 A1 | 10/2005 | Foley et al. | |
| 2005/0240239 A1 | 10/2005 | Bojeva et al. | |
| 2005/0240279 A1 | 10/2005 | Kagan et al. | |
| 2005/0245957 A1 | 11/2005 | Starkebaum et al. | |
| 2005/0246037 A1 | 11/2005 | Starkebaum | |
| 2005/0250979 A1 | 11/2005 | Coe | |
| 2005/0256587 A1 | 11/2005 | Egan | |
| 2005/0267405 A1 | 12/2005 | Shah | |
| 2006/0015151 A1 | 1/2006 | Aldrich | |
| 2006/0020247 A1 | 1/2006 | Kagan et al. | |
| 2006/0030949 A1 | 2/2006 | Geitz | |
| 2006/0074450 A1 | 4/2006 | Boveja et al. | |
| 2006/0079944 A1 | 4/2006 | Imran | |
| 2006/0089571 A1 | 4/2006 | Gertner | |
| 2006/0129027 A1 | 6/2006 | Catona | |
| 2006/0129094 A1 | 6/2006 | Shah | |
| 2006/0161172 A1 | 7/2006 | Levine et al. | |
| 2006/0206063 A1 | 9/2006 | Kagan et al. | |
| 2006/0206064 A1 | 9/2006 | Kagan et al. | |
| 2006/0206160 A1 | 9/2006 | Cigaina et al. | |
| 2006/0249165 A1 | 11/2006 | Silverman et al. | |
| 2006/0253142 A1 | 11/2006 | Bjerken | |
| 2006/0257444 A1 | 11/2006 | Tropsha et al. | |
| 2006/0257445 A1 | 11/2006 | Tropsha et al. | |
| 2006/0257446 A1 | 11/2006 | Tropsha et al. | |
| 2006/0282107 A1 | 12/2006 | Hashiba et al. | |
| 2006/0293742 A1 | 12/2006 | Dann et al. | |
| 2007/0004963 A1 | 1/2007 | Benchetrit | |
| 2007/0010794 A1 | 1/2007 | Dann et al. | |
| 2007/0010864 A1 | 1/2007 | Dann et al. | |
| 2007/0010865 A1 | 1/2007 | Dann et al. | |
| 2007/0010866 A1 | 1/2007 | Dann et al. | |
| 2007/0021761 A1 | 1/2007 | Phillips | |
| 2007/0038308 A1 | 2/2007 | Geitz | |

* cited by examiner

CAUTERY CATHETER

RELATED APPLICATION

This application claims the benefit of priority from U.S. provisional application No. 60/689,672 filed Jun. 10, 2005, which is incorporated herein by reference.

TECHNICAL FIELD

The invention generally relates to a cautery catheter device.

BACKGROUND

A variety of medical problems require cauterization, which is the burning, scarring, or cutting of tissue by means of heat, cold, electric current, or caustic chemicals. For example, during surgery bleeding from severed arteries may be stemmed by cautery, or tissue may be cut with a cautery cutter to reduce the bleeding that may occur with a non-cauterizing tissue cutter.

Providing a cauterizing capability within a medical device is often conveniently accomplished by including one or more electrical conductors that may be placed in contact with tissue at a treatment site to form an electrical circuit that includes the tissue. When high frequency current is activated within the circuit, via an attached electrocautery generator, tissue is heated and cauterized. Such devices are known as electrocautery devices.

In flexible gastrointestinal (GI) endoscopy, catheter-based electrocautery devices are often used for various treatments. For example, an electrocautery snare provides a conductive wire loop that may be used to lasso a polyp in the colon and cut tissue at the base of the polyp in order to resect it. Electrocautery snares are often used in the esophagus to remove dysplastic mucosal tissue, known as Barrett's Esophagus, which can become cancerous if untreated. An electrocautery probe includes a small head, with exposed electrodes, that may be placed in contact with tissue to cauterize very small areas. Such probes are often used to stem small bleeding sites throughout the GI tract. Biopsy forceps include electrified cups that cauterize tissue as small samples are collected. Electrocautery sphincterotomes include an electrified, tensionable cutting wire to controllably cut the Sphincter of Otti, along a prescribed plane, to improve access to the biliary and pancreatic ductal systems.

Cautery devices available for use during flexible GI endoscopy, such as the snares, probes, forceps, and sphincterotomes described above, are not well suited for cauterizing large surface areas, such as large sections of Barrett's Esophagus, large bleeding sites such as a large gastric ulcer, or following resection of a large sessile polyp. Use of the available devices to treat such areas often requires repeated cauterizations, which can unreasonably increase the procedure time and need for sedation. Moreover, of the other currently available cautery devices, such as scalpels, clamps, staplers and scissors, that may be capable of treating large areas of tissue, none are generally adapted to fit through the accessory channel of a flexible GI endoscope.

In view of the drawbacks of the current technology, there is an unmet need for a cautery catheter that can fit through an endoscope accessory channel and which can rapidly and effectively cauterize treatment sites having relatively large surface areas.

SUMMARY

Accordingly, it is an object of the present invention to provide a cautery catheter that resolves or improves upon one or more of the above-described drawbacks.

In one aspect, a cautery catheter is disclosed. The cautery catheter includes a catheter having an electrically conductive mesh attached at its distal portion. A control handle assembly includes a spool and stem which are provided to control the position of the mesh. The mesh is attached to the surface of the catheter at the distal portion of the catheter. The control handle assembly is connected to the proximal end of the catheter. Pushing the spool while pulling the stem causes a drive wire to become compressed. The drive wire transmits the compressive force to the mesh. Compression of the mesh causes it to transform into a bow-shaped configuration by shortening in length and increasing in width. The bow-shaped configuration of the mesh causes the mesh to be positioned against the treatment site. An electrocautery unit supplies the required electrical energy to perform cauterization at the treatment site.

In a second aspect, a cautery catheter with a balloon is disclosed. The cautery catheter includes a catheter having an electrically conductive mesh attached at its distal portion. A balloon is provided to control the expansion of the mesh. The balloon is positioned between the outer catheter surface and the mesh. Inflation of the balloon causes the mesh to expand into a bow-shaped configuration adjacent a treatment site. An electrocautery unit supplies the required electrical energy to perform cauterization at the treatment site.

In a third aspect, a method for cauterizing a treatment site is disclosed. A cautery catheter is disclosed having a catheter, an electrically conductive mesh, and an electrically conductive drive wire. The distal portion of the catheter is advanced to the treatment site and the mesh is expanded so as to be brought into contact with the treatment site. An electrocautery unit supplies electrical energy to the expanded mesh to cauterize the treatment site.

BRIEF DESCRIPTION OF THE DRAWINGS

Embodiments of the present invention will now be described by way of example with reference to the accompanying drawings, in which.

DETAILED DESCRIPTION OF THE DRAWINGS AND THE PRESENTLY PREFERRED EMBODIMENTS

Figure 1:
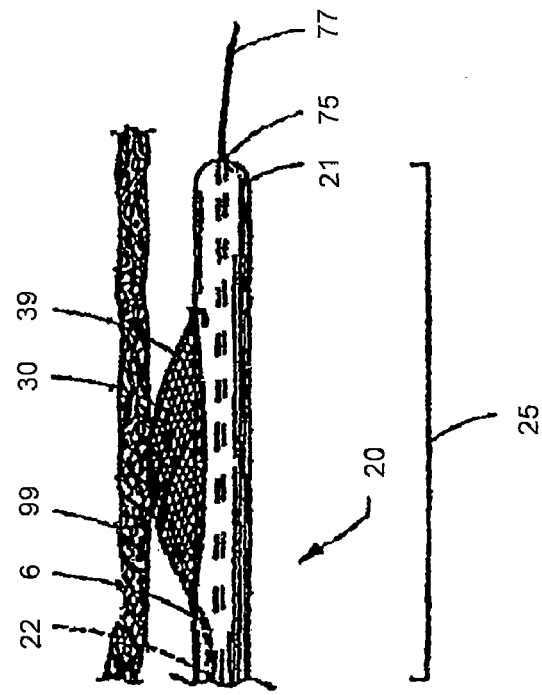
FIG. 1 is a side view of a cautery catheter in accordance with the present invention illustrating a cautery mesh in an expanded state and against a desired treatment site for cauterizing.
Figure 1:
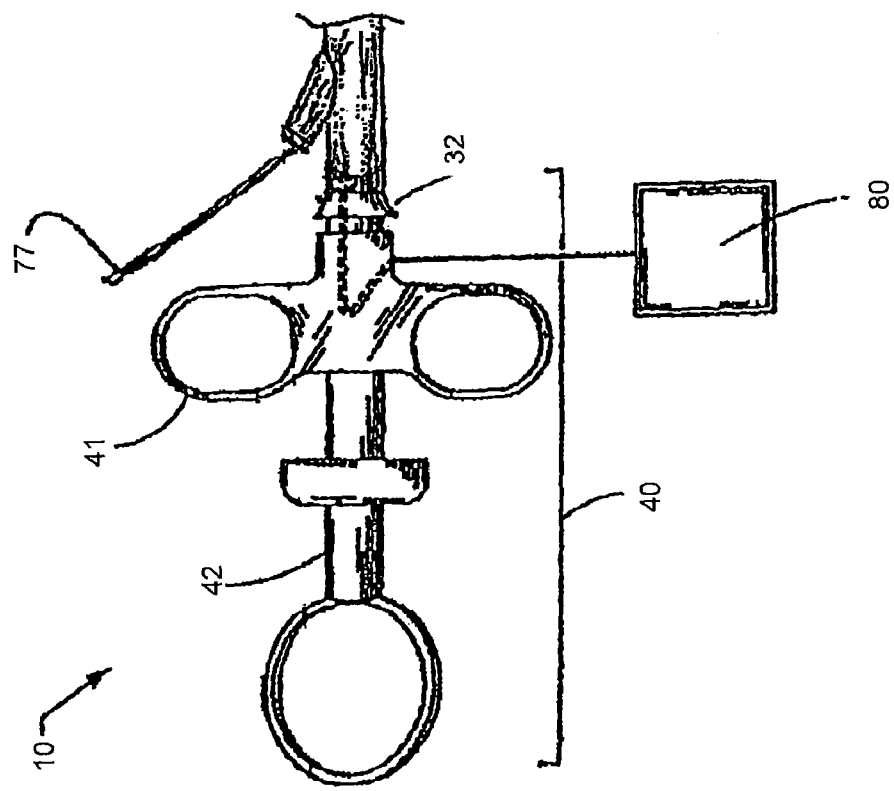

The invention is described with reference to the drawings in which like elements are referred to by like numerals. The relationship and functioning of the various elements of this invention are better understood by the following detailed description. However, the embodiments of this invention as described below are by way of example only, and the invention is not limited to the embodiments illustrated in the drawings. It should also be understood that the drawings are not to scale and in certain instances details, which are not necessary for an understanding of the present invention, have been omitted such as conventional details of fabrication and assembly.

FIG. 1 illustrates a cautery catheter 10. Cautery catheter 10 includes catheter 20 having distal portion 25 and proximal end 32, mesh 30, and control handle assembly 40. Distal portion 25 of catheter 10 includes electrically conductive mesh 30. Expansion of mesh 30 is controlled by drive wire 22. Drive wire 22 is actuated by control handle assembly 40. In general, cautery catheter 10 can be used for cauterizing sections having a large surface area. Actuation of drive wire 22 by control handle assembly 40 causes mesh 30 to expand adjacent treatment site 99. An electrocautery unit 80 supplies electrical energy to expanded mesh 30 to enable cauterization of treatment site 99.

Figure 2:
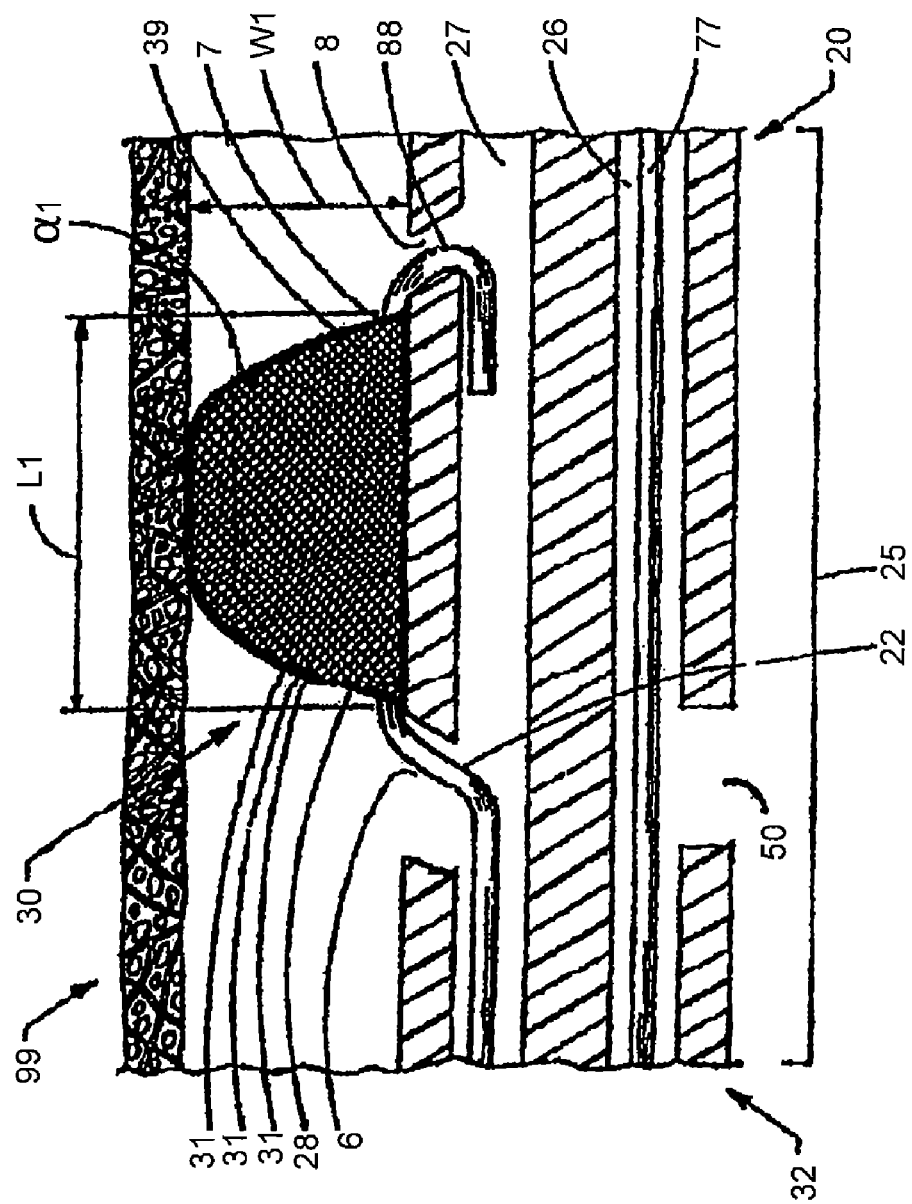
FIG. 2 is a cross-sectional side view of the distal portion of the cautery catheter of FIG. 1 illustrating the mesh expanded into contact with a treatment site to be cauterized.

FIG. 2 illustrates a cross-sectional view of the distal portion 25 of catheter 20 with the mesh 30 expanded into contact with a treatment site to be cauterized. Catheter 20 includes lumens 26 and 27. Lumen 27 provides a passageway for drive wire 22 to be movably disposed. Lumen 26 extends along the entire longitudinal length of catheter 20 and provides a passageway through which guide wire 77 can be passed to the treatment site. Lumen 26 terminates in distal exit port 75 at catheter distal end 21, as shown in FIG. 1. Cautery catheter 10 can be loaded onto and advanced along guide wire 77 to ensure accurate positioning of cautery catheter 10 at treatment site 99. It should be understood that catheter 20 is not required to have lumen 26 through which guide wire 77 passes. In an alternative embodiment, catheter 20 can be deployed to the treatment site without being loaded onto guide wire 77 (not shown). Likewise, it should be understood that guide wire lumen 26 may only extend through a portion of catheter 20, for example, through distal portion 25 only.

Additionally, a side port 50, as shown in FIG. 2, could be included along the distal portion 25 through the side wall of the catheter 20. The side port 50 would be in communication with guide wire lumen 26 through which the guide wire 77 could pass therethrough so as to use the catheter 20 in a rapid exchange, short wire, or ultra-short wire mode of operation.

Catheter 20 is a flexible tubular member and may be formed from any semi-rigid polymer. For example, catheter 20 can be formed from polyurethane, polyethylene, tetrafluoroethylene, polytetrafluoroethylene, perfluoalkoxl, fluorinated ethylene propylene, or the like. In the embodiment illustrated, the compressive force required to expand mesh 30 is generally not sufficient to bend distal portion 25 of catheter 20. This is because catheter 20 is relatively more rigid than mesh 30. Distal portion 25 of catheter 20 does not incur substantial bending moment. As a result, distal portion 25 of catheter 20 remains relatively straight during expansion of mesh 30, as shown in FIG. 1.

Distal portion 25 of catheter 20 is attached to mesh 30, as illustrated in FIG. 2. Mesh 30 is formed from a series of conductive filaments 31 loosely interwoven together. Filaments 31 of mesh 30 are formed from any metal or metal alloy, such as stainless steel. Filaments 31 can also be metal coated. The ends of filaments 31 at distal end 39 of mesh 30 are soldered to a short anchor wire 88. Anchor wire 88 proceeds through side wall opening 8 and into lumen 27. Anchor wire 88 is stabilized in lumen 27 with an anchor (not shown). Anchor wire 88 is not required to be electrically conductive. The ends of filaments 31 at proximal end 28 of mesh 30 are soldered to drive wire 22, which extends out of lumen 27 through side wall opening 6. Side wall opening 6, in the embodiment illustrated, comprises an elongated slot to provide longitudinal movement for the drive wire 22 as the drive wire 22 expands or collapses the mesh 30.

Figure 3:
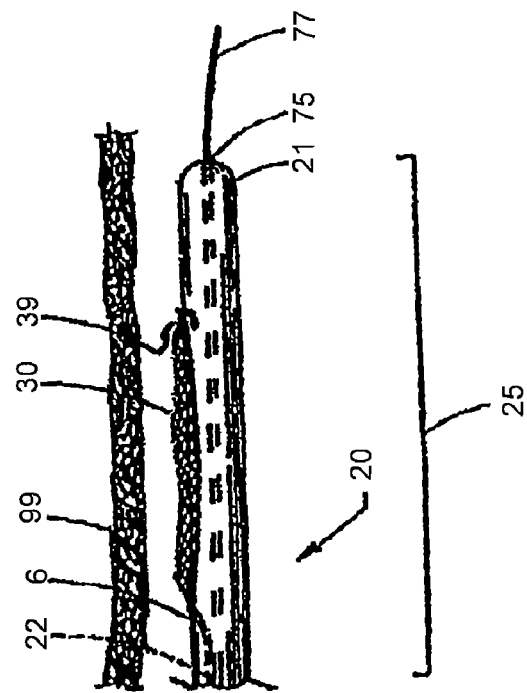
FIG. 3 is a side view of the cautery catheter of FIG. 1 illustrating the mesh in an unexpanded state.
Figure 3:
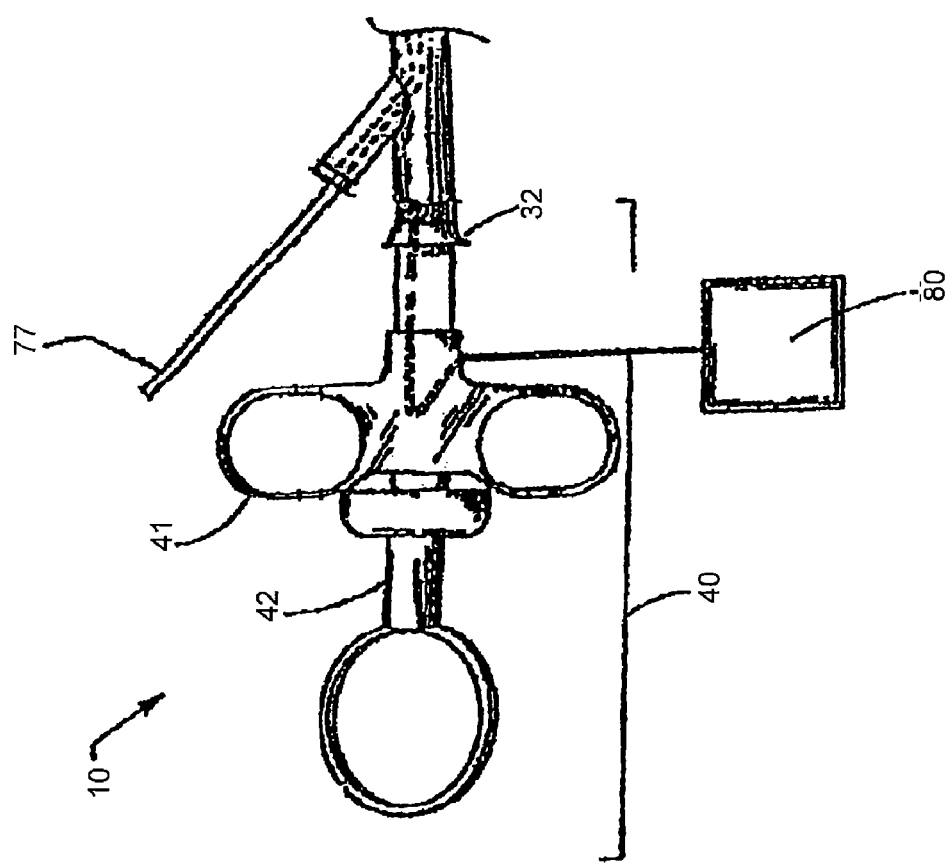
Figure 5:
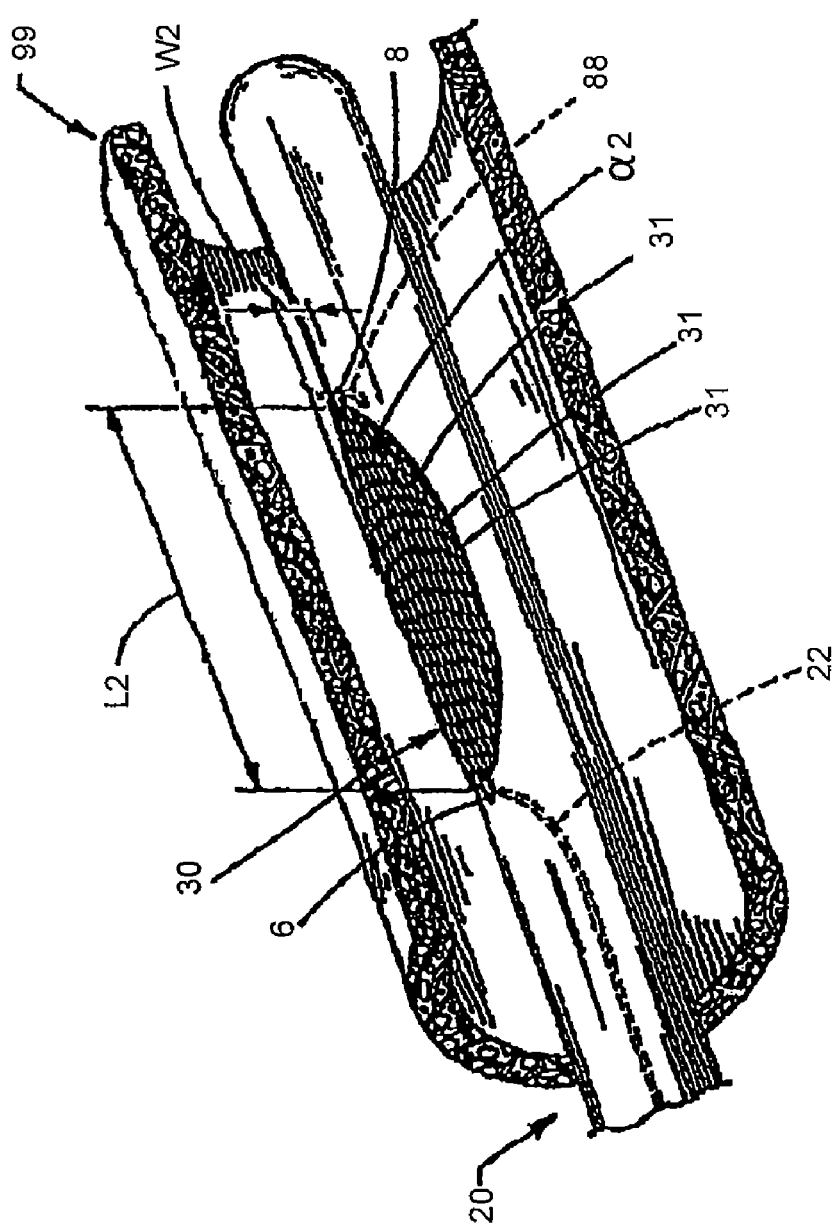
FIG. 5 is a perspective view of the distal portion of a cautery catheter of FIG. 3 illustrating the mesh in an unexpanded state and disposed against the outer surface of the catheter.

FIG. 5 illustrates a perspective view of the distal portion 25 of cautery catheter 10 of FIG. 3 showing the mesh 30 in an unexpanded state and disposed against the outer surface of the catheter 20. Mesh 30 lays substantially flat and aligned on catheter 20 surface. Mesh 30 has length $L_2$ and width $W_2$ where $L_2$ is substantially greater than $W_2$. The angle between vertical and horizontal filaments 31, $\alpha_2$, is substantially acute. Alignment of mesh 30 with the longitudinal axis of catheter 20 in the unexpanded state facilitates insertion of cautery catheter 10 through the working channel of a duodenoscope, colonoscope, gastroscope, or other conventional endoscope (not shown).

FIG. 2 shows mesh 30 in an expanded state adjacent to treatment site 99. Mesh 30 is in a bow-shaped configuration. Length $L_1$ of mesh 30 is comparable to width $W_1$ of mesh 30. More specifically, length $L_1$ of expanded mesh 30 has decreased relative to length $L_2$ of unexpanded mesh 30 (FIG. 5). Additionally, width $W_1$ of expanded mesh 30 (FIG. 2) has increased relative to width $W_2$ of unexpanded mesh 30 in its unexpanded state (FIG. 5). The angle between vertical and horizontal filaments 31, $\alpha_1$, is substantially orthogonal when the mesh 30 is in its expanded state. The effective surface area of mesh 30, when in the expanded state, facilitates cauterization of relatively large tissue regions in a relatively short period of time.

Expansion of mesh 30 is controlled by drive wire 22. Drive wire 22 is an electrical conductor for cautery catheter 10, and in particular, mesh 30. The proximal end of drive wire 22 is secured to control handle assembly 40 (FIG. 3). The distal end of drive wire 22 is soldered to proximal end 28 of mesh 30 at sidewall opening 6 (FIG. 2).

Drive wire 22 is actuated by control handle assembly 40. FIG. 3 illustrates a side view of the cautery catheter 10 of FIG. 1 illustrating the mesh 30 in an unexpanded state. Control handle assembly 40 includes stem 42 and spool 41. Distal end of stem 42 is connected to proximal end 32 of catheter 20. Stem 42 includes a lumen through which drive wire 22 is disposed. Spool 41 is slidably engaged with stem 42. Spool 41 is provided with a range of slidable motion along stem 42. Thus, movement of the spool 41 relative to the stem 42 causes drive wire 22 to move relative to the catheter 20. It should be understood that other configurations of control handle assembly 40 can be employed to actuate drive wire 22.

Figure 4:
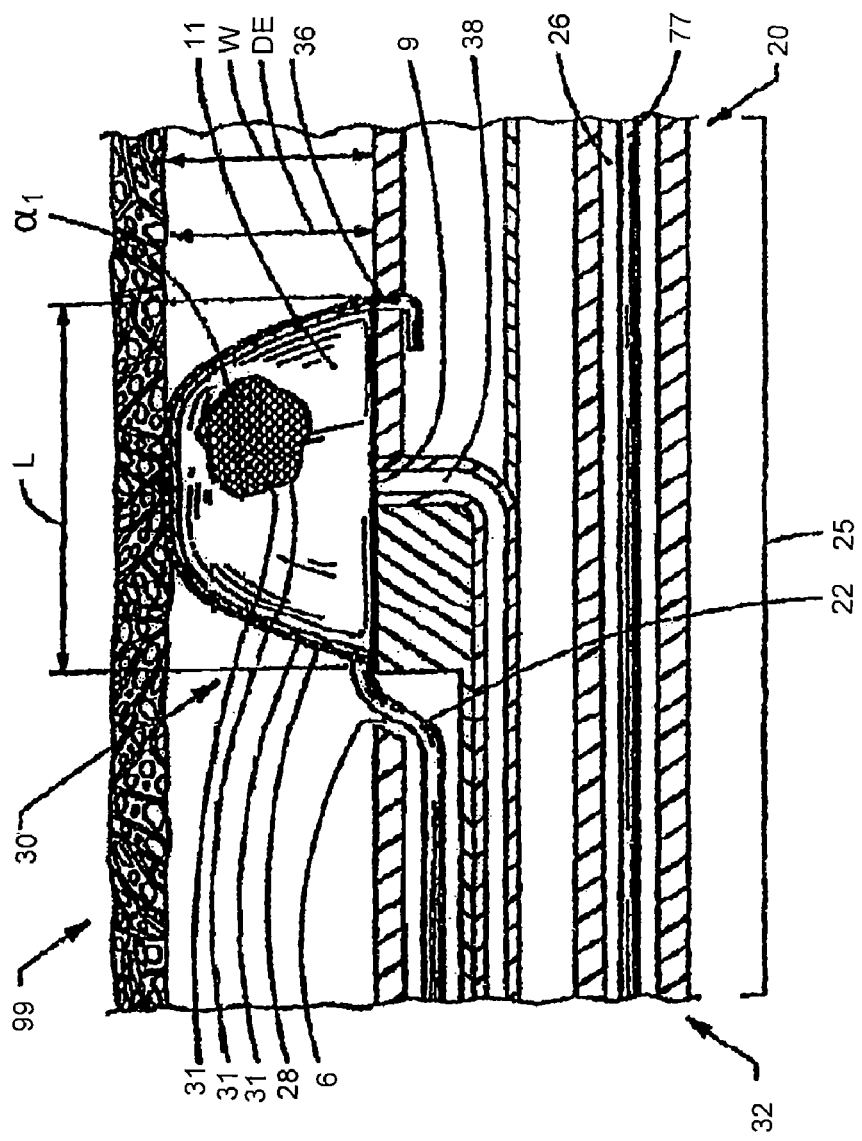
FIG. 4 is a cross-sectional view of the distal portion of an alternative embodiment of a cautery catheter in accordance with the present invention having an inflatable balloon that is used to expand a cautery mesh against a treatment site for cauterization.

In accordance with another embodiment of the present invention, FIG. 4 illustrates a partial cross-sectional view of catheter 20 having balloon 36. Balloon 36 provides an alternative or supplemental mechanism for expanding mesh 30 adjacent treatment site 99. Balloon 36 is positioned externally and along distal portion 25 of catheter 20. Balloon 36 underlies mesh 30. For clarity purposes, a section of the balloon 36 is cut-away to expose the mesh 30 which overlies the balloon 36. Balloon 36 is shown inflated against mesh 30 to expand it against treatment site 99. Lumen 38 extends from proximal end 32 of catheter 20 through sidewall opening 9 of catheter 20 and into interior 11 of balloon 36. Distal end of drive wire 22 is soldered to proximal end 28 of mesh 30 at sidewall opening 6. Drive wire 22 acts as a conductive path for electric current from electrocautery unit 80 (FIG. 1) to mesh 30.

A procedure for using cautery catheter 10 will now be described. Pushing spool 41 from the proximal position (as shown in FIG. 3) to the distal position (as shown in FIG. 1) while pulling stem 42 of control handle assembly 40 transmits a compressive force to drive wire 22. Drive wire 22 transmits the compressive force to filaments 31 of mesh 30 at proximal end 28 of mesh. Compression of filaments 31 causes mesh 30 to transform into a bow-shaped configuration that projects outwardly towards treatment site 99, as shown in FIGS. 1 and 2. In particular, mesh 30 shortens in length $L_1$ and correspondingly increases in width $W_1$, as FIG. 2 illustrates. The angle, $\alpha$, between vertical and horizontal filaments 31 of mesh 30 changes from substantially acute in the uncompressed state ($\alpha_2$ of FIG. 5) to substantially orthogonal in the compressed state ($\alpha_1$ of FIG. 2). Such geometric changes of mesh 30 increase the effective surface area of mesh 30. Once mesh 30 has been expanded into a bowed-shape configuration against treatment site 99, mesh 30 can be electrically energized via electrocautery unit 80, as shown in FIG. 1, to cauterize tissue at treatment site 99. Standard electrosurgical techniques as are known to one of ordinary skill in the art may be used to cauterize the tissue.

After treatment site 99 has been cauterized, spool 41 is retracted from the distal position (as shown in FIG. 1) to the proximal position (as shown in FIG. 3) as stem 42 is simultaneously pushed, thereby alleviating the compressive force exerted by drive wire 22 on mesh 30. Removal of the compressive force causes filaments 31 of mesh 30 to reorient to the configuration of FIG. 5 in which mesh 30 lays substantially flat against surface of catheter 20. Additionally, length $L_2$ of mesh 30 increases as width $W_2$ of mesh 30 decreases. The angle, $\alpha_2$, between vertical and horizontal filaments 31 is substantially acute.

As an alternative to or in addition to placing mesh 30 in compression with control handle assembly 40 (shown in FIGS. 1 and 2) catheter 20 of FIG. 4 can be used to inflate balloon 36 against mesh 30, thereby expanding mesh 30 against treatment site 99. More specifically, fluid is forced through an entrance port (not shown) of inflation lumen 38 with, for example, a conventional syringe attached to a Luer lock fitting (not shown), through sidewall opening 9, and into the interior of balloon 11 to cause balloon 36 to inflate to a diameter $D_E$, as shown in FIG. 4. As balloon 36 inflates to diameter $D_E$, balloon 36 exerts an outwardly directed force against the interior of mesh 30. In particular, inflation of balloon 30 pushes the center portion of mesh 30 away from the surface of catheter 20. Orientation of filaments 31 changes from an acute angle $\alpha_2$ (FIG. 5) to an orthogonal angle $\alpha_1$ (FIG. 4). Such reorientation of filaments 31 enables mesh 30 to increase its effective surface area by shortening in length L and increasing in width W. Effective surface area of mesh 30 continues to increase until mesh 30 is adjacent to desired treatment site 99. With mesh 30 in contact with treatment site 99, electrocautery unit 80 supplies electrical energy to filaments 31 of mesh 30 to enable cauterization. The localized heating effect of tissue within treatment site 99 at the point of contact with mesh 30 does not cause appreciable thermal degradation of balloon 36.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims. For example, the invention has been described in the context of cauterizing regions within the gastrointestinal tract. Application of the principles of the invention to access other body lumens are within the ordinary skill in the art and are intended to be encompassed within the scope of the attached claims. Moreover, in view of the present disclosure, a wide variety of cautery catheters containing electrically conductive meshes and methods of their uses will become apparent to one of ordinary skill in the art.

The invention claimed is:

1. A medical instrument, comprising:
    a catheter having a proximal portion, a distal portion and a central longitudinal axis extending between the proximal and the distal portions;
    an electrically conductive mesh disposed along an outer surface of the distal portion of the catheter, wherein the mesh is asymmetrically disposed relative to the central longitudinal axis and does not extend circumferentially about a substantial portion of the catheter, and further wherein the mesh is spaced away from and does not encompass the central longitudinal axis; and
    a connector disposed on the proximal portion of the catheter, the connector being conductively connected to the mesh, the connector being configured for a connection to a power source for supplying a current sufficient to electrify the mesh.

2. The medical instrument of claim 1, further comprising:
    an electrically conductive wire extending from the proximal portion to the mesh; and
    a control handle operably connected to the proximal portion of the catheter.

3. The medical instrument of claim 2, wherein the electrically conductive wire comprises a control wire configured for manipulation of the mesh.

4. The medical instrument of claim 1, wherein the mesh is configured to move between a first position and a second position, wherein in the first position the mesh is substantially adjacent to the catheter, and wherein in the second position a portion of the mesh is further spaced away from the outer surface of the catheter.

5. The medical instrument of claim 4, further comprising an apparatus for moving the mesh between the first position and the second position.

6. The medical instrument of claim 5, wherein the apparatus for moving the mesh comprises a control wire operably connected to a handle.

7. The medical instrument of claim 1, wherein the mesh is configured to move between a first position and a second position, wherein in the first position the mesh is substantially spaced a first distance from the central longitudinal axis of the catheter, and wherein in the second position at least a portion of the mesh is spaced a second distance from the central longitudinal axis of the catheter, the second distance being greater than the first distance.

8. The medical instrument of claim 7, wherein the mesh comprises a plurality of interwoven electrically conductive filaments.

9. The medical instrument of claim 8, wherein a control handle comprises a stem and a spool slidably attached to the stem, wherein one of the stem and the spool is operably connected to the mesh such that sliding the stem relative to the spool causes an angle between the filaments to change.

10. The medical instrument of claim 8, wherein the filaments are formed from stainless steel.

11. The medical instrument of claim 8, wherein the filaments are formed from nitinol.

12. The medical instrument of claim 1, further comprising a balloon operably connected to the catheter, the balloon being disposed between the catheter and the mesh.

13. The medical instrument of claim 12, wherein the balloon is expandable from a first contracted position to a second expanded position, wherein in the first position the mesh is substantially adjacent to the catheter, and wherein in the second position a portion of the mesh is spaced away from the catheter.

14. The medical instrument of claim 13, wherein in the second position, the portion of the mesh spaced away from the catheter is engaged by a portion of the balloon.

15. The medical instrument of claim 12, wherein the mesh is formed from nitinol.

16. The medical instrument of claim 12, wherein the mesh is formed from stainless steel.

17. A method for cauterizing a treatment site, comprising the steps of:
   (a) providing a medical instrument, comprising:
      a catheter having a proximal portion and a distal portion, and a central longitudinal axis extending between the proximal and the distal portions;
      an electrically conductive mesh operably connected to the distal portion of the catheter, wherein the mesh is configured to radially bow outwards asymmetrically relative to the central longitudinal axis, the mesh being disposed to one side of a plane intersecting the central longitudinal axis; and
      an energy source operably connected to the mesh, wherein activating the energy source energizes the mesh;
   (b) advancing the distal portion of the catheter to the treatment site;
   (c) contacting the treatment site with the mesh; and
   (d) activating the energy source to cauterize the treatment site.

18. The method of claim 17, further comprising the steps of:
   (e) locating a second treatment site;
   (f) positioning the distal portion of the catheter adjacent the second treatment site; and
   (g) reactivating the energy source to cauterize the second treatment site.

19. The method of claim 17, wherein the step (c) of contacting the treatment site with the mesh comprises the step of expanding the mesh outwardly from the catheter.

20. The method of claim 19, wherein the medical instrument further comprises a balloon operably connected to the catheter, the balloon being disposed between the catheter and the mesh.

21. The method of claim 20, further comprising the step of inflating the balloon with a fluid so as to contact the treatment site with the mesh.

22. The method of claim 17, further comprising the steps of:
   (e) deflating the balloon;
   (f) locating a second treatment site;
   (g) positioning the distal portion of the catheter adjacent the second treatment site;
   (h) reinflating the balloon so as to contact the second treatment site with the mesh; and
   (i) activating the energy source to cauterize the second treatment site.

23. A medical instrument, comprising:
   a catheter having a proximal portion, and a distal portion and a central longitudinal axis extending between the proximal portion and the distal portion, the distal portion having a first side and a second side disposed on opposite sides of the central longitudinal axis;
   an electrically conductive mesh disposed on the distal portion of the catheter adjacent to the first side, the mesh being deformable from a collapsed configuration substantially disposed along an outer surface of the catheter to an expanded configuration, wherein a central portion of the mesh is spaced away from the surface of the catheter in the expanded configuration, wherein the mesh is asymmetrically disposed relative to and spaced away from the central longitudinal axis, and wherein second side of the distal portion of the catheter is not enclosed within the mesh; and
   a connector disposed on the proximal portion of the catheter, the connector being conductively connected to the mesh by a control wire, the control wire disposed through a lumen of the catheter, the connector being configured for a connection to a power source for supplying a current sufficient to electrify the mesh.

24. The medical instrument of claim 23, wherein the mesh comprises a plurality of interwoven electrically conductive filaments.

25. The medical instrument of claim 24, wherein a control handle comprises a stem and a spool slidably attached to the stem, wherein one of the stem and the spool is operably connected to the mesh such that sliding the stem relative to the spool causes an angle between the filaments to change.

26. The medical instrument of claim 23, further comprising a balloon operably connected to the catheter, the balloon being disposed between the catheter and the mesh, wherein the balloon is expandable from a first contracted position to a second expanded position, wherein in the first position the mesh is substantially adjacent to the catheter, and wherein in the second position a portion of the mesh is spaced away from the catheter.

* * * * *

UNITED STATES PATENT AND TRADEMARK OFFICE
CERTIFICATE OF CORRECTION

PATENT NO. : 7,967,818 B2  Page 1 of 1
APPLICATION NO. : 11/450078
DATED : June 28, 2011
INVENTOR(S) : Kenneth C. Kennedy, II It is certified that error appears in the above-identified patent and that said Letters Patent is hereby corrected as shown below:

In the Claims

Column 8, claim 23, line 8, after "a proximal portion," delete "and".

Signed and Sealed this
Thirtieth Day of August, 2011

David J. Kappos
*Director of the United States Patent and Trademark Office*